United States Patent [19]

Schutt

[11] 4,393,140

[45] Jul. 12, 1983

[54] PROCESS FOR THE PREPARATION OF THE HIGHLY PURE ENZYME KALLIKREIN FROM SWINE PANCREAS EXTRACTS

[75] Inventor: Hermann Schutt, Wuppertal, Fed. Rep. of Germany

[73] Assignee: Bayer Aktiengesellschaft, Leverkusen, Fed. Rep. of Germany

[21] Appl. No.: 339,017

[22] Filed: Jan. 12, 1982

[30] Foreign Application Priority Data

Jan. 31, 1981 [DE] Fed. Rep. of Germany ....... 3103257

[51] Int. Cl.³ .............................................. C12N 9/64
[52] U.S. Cl. ..................................... 435/226; 435/815
[58] Field of Search ......................................... 435/226

[56] References Cited

U.S. PATENT DOCUMENTS

| | | | |
|---|---|---|---|
| 3,100,736 | 8/1963 | Werle et al. | 424/95 |
| 3,660,237 | 5/1972 | Schultz | 435/226 |
| 3,905,870 | 9/1975 | Kutzbach et al. | 435/226 |
| 4,038,141 | 7/1977 | Tokuyasu et al. | 435/226 |
| 4,252,902 | 2/1981 | Fuji et al. | 435/226 X |

OTHER PUBLICATIONS

Methods in Enzymology, vol. 45, pp. 289–303, (1976).

*Primary Examiner*—Lionel M. Shapiro
*Attorney, Agent, or Firm*—Sprung, Horn, Kramer & Woods

[57] ABSTRACT

The invention relates to a process for the preparation of the highly pure enzyme kallikrein from organ extracts, in particular from swine pancreas extracts, the accompanying proteolytic activity of the swine pancreas extract being separated off by chromatography on ion exchangers and the highly pure enzyme kallikrein being obtained by chromatography on support materials with a kallikrein-trypsin inhibitor (basic pancreatic trypsin inhibitor=BPTI) covalently bonded in a particular manner.

5 Claims, No Drawings

PROCESS FOR THE PREPARATION OF THE HIGHLY PURE ENZYME KALLIKREIN FROM SWINE PANCREAS EXTRACTS

The present invention relates to a process for the preparation of the highly pure enzyme kallikrein from organ extracts, in particular from swine pancreas extracts, the accompanying proteolytic activity of the swine pancreas extract being separated off by chromatography on ion exchangers and the highly pure enzyme kallikrein being obtained by chromatography on support materials with a kallikrein-trypsin inhibitor (basic pancreatic trypsin inhibitor=BPTI) covalently bonded in a particular manner.

The enzyme kallikrein and its biochemical properties have been described by F. Fiedler, Methods in Enzymology, volume 45, Proteolytic Enzymes, Part B, 289-303.

When kallikrein acts on endogenous kininogen, the physiologically active kinins (for example kallidin) are liberated. Kallikrein preparations are therefore used therapeutically (E. K. Frey, H. Kraut and E. Werle, Das Kallikrein-Kinin-System und seine Inhibitoren (The Kallikrein/kinin system and its inhibitors), F. Enke, Stuttgart (1968), 150 et seq.).

The enzyme kallikrein has already been obtained as a single compound from pre-purified extracts of the swine pancreas by chromatography on ion exchanger columns (C. Kutzbach and G. Schmidt-Kastner, Hoppe-Seyler's Z. Physiol. Chem. 353 (1972), 1099-1106, DE-AS (German Published Specification) 2,154,556 and DE-OS (German Published Specification) 2,154,557).

However, the processes mentioned are non-specific and industrially expensive, since, starting from the organ extract, a total of 5 steps are necessary in order to obtain the pure enzyme kallikrein. The technique of affinity chromatography, which consists of the biospecific interaction between an inhibitor and an enzyme, in theory succeeds with one isolation step and has therefore recently become the aim as a preferred method for isolating enzymes on an industrial scale.

Various affinity chromatography processes for kallikrein which are based on the interaction of carrier-bonded BPTI with kallikrein have already been disclosed in the literature.

BPTI reversibly forms an enzyme-inhibitor complex with kallikrein, depending on the pH value used (H. Tschesche, Angewandte Chemie 86 (1974), 24-40 and E. Auhagen, International Symposium on Drugs of Animal Origin, A. Leonardi and J. Walsh ed., Ferro edizioni Mailand page 69).

Compared with other polyvalent inhibitors, for example the soya bean-trypsin inhibitor, BPTI is particularly suitable for isolating proteolytic enzymes from organ extracts because of its stability to changes in pH and to temperature, its proteolytic stability and its stability to solvents (B. Kassell, Methods in Enzymology 19 (1970), 844-852). As a result of being bonded to the BPTI, the proteolytic enzyme is largely protected from inactivation.

BPTI is a polypeptide with 58 aminoacids of known primary structure and is obtained from bovine organs (B. Kassell and M. Laskowski, Biochem. Biophys. Res. Commun. 20 (1965), 463-468 and F. A. Anderer and S. Hörnle, J. Biol. Chem. 241 (1966), 1568-1572).

According to D. A. Johnson and J. Travis, Anal. Biochem. 72 (1976), 573-576, G. J. Baugh and J. Travis, Biochemistry 15 (1976), 836-841, R. Geiger, W. Stuckstedte and H. Fritz, Hoppe-Seyler's Z. Physiol. Chem. 361 (1980), 1003-1016 and DE-OS (German Published Specification) 2,363,201, BPTI has been covalently bonded to supports which contain hydroxyl groups and are activated with cyanogen bromide and has been employed for affinity chromatography of proteolytic enzymes.

Furthermore, for the purpose of affinity chromatography, covalent bonding of BPTI to anhydride resins has been disclosed in DE-OS (German Published Specification) 1,768,934 and by H. Fritz, B. Brey, A. Schmal and E. Werle, Hoppe-Seyler's Z. Physiol. Chem. 350 (1969), 617-625, and covalent bonding of BPTI by means of water-soluble carbodiimides on Sepharose 4 B carrying carboxyl groups has been disclosed by G. R. Geiger, R. Mann and T. Bettels, J. Clin. Chem. Biochem. 15 (1977), 479-483, O. Ole-Moi Yoi, J. Spragg and K. F. Austen, J. Immunol. 121 (1978), 66-71, N. B. Oza and R. W. Ryan, Biochem. J. 171 (1978), 285-288 and N. B. Oza, V. M. Amin, R. K. McGregor, A. G. Scidi and D. A. Carretero, Biochem. Pharmacol. 25 (1976), 1607-1612.

However, the processes which have been disclosed have considerable disadvantages which severely restrict their economical application.

Thus, purification of enzymes by affinity chromatography is not solely dependent on the biospecific interaction of the effector (inhibitor) with the enzyme to be isolated, but the profitability of the process also depends to a considerable extent on the coupling method used for the effector and on the chemical structure of the polymeric carrier.

Thus, it has been disclosed, for example, that the isourea bond formed after the carrier containing hydroxyl groups has been activated with cyanogen bromide is cationically charged and unstable (G. I. Tesser, H. U. Fisch and R. Schwyzer, Helvetica chimica acta 57 (1974), 1718-1730).

An anionic BPTI-carrier which must be neutralised with diamines for isolation of kallikrein is obtained in DE-OS (German Published Specification) No. 1,768,934. No stable BPTI-carrier and no pure kallikrein is obtained by either procedure. The procedure of DE-OS (German Published Specification) No. 2,363,201 also has disadvantages and is uneconomic. A swine pancreas extract is worked up, without preliminary purification, on a BPTI-"Sepharose" 4 B (Trade Mark) column to give trypsin chymotrypsin and kallikrein. Trypsin and chymotrypsin are substantially cheaper than kallikrein. However, in order to isolate kallikrein from trypsin-containing swine pancreas extract, most of the extremely expensive BPTI-"Sepharose" 4 B is used to isolate the cheap trypsin, since on the one hand the concentration of trypsin and chymotrypsin in swine pancreas is about 100 times greater than that of kallikrein (C. Kutzbach and G. Schmidt-Kastner, Kininogenases F. K. Schattauer-Verlag, Stuttgart-New York (1973), 23-25) and on the other hand the trypsin-BPTI complex (for bovine trypsin: $K_i = 6.0 \times 10^{-14}$ M at pH 8.0, M. Lazdunski, J. B. Vincent, H. Schweitz, M. Peron-Renner and J. Pudlers (1974) in Proteinase Inhibitors-Bayer Symposium V (H. Fritz, H. Tschesche, and L. J. Greene, E. Truscheit editors 420-431, Springer-Verlag, Berlin)), is considerably less dissociated than the kallikrein-BPTI complex (for swine pancreas kallikrein, $K_i = 1 \times 10^{-9}$ M at pH 8.0, H. Fritz, H. Schult, R. Meister and E. Werle, Hoppe-Seyler's Z. Physiol. Chem. 350 (1969), 1531–1540). An improved process for the preparation of pure kallikrein has now been found.

According to the present invention there is provided a process for the preparation of pure kallikrein, in which an organ extract containing kallikrein is adjusted to a conductivity of 2 to 6 mScm$^{-1}$ at a pH value of 5 to 8, the organ extract thus prepared is brought into contact with an ion exchanger in batch form or column form, the kallikrein is eluted by continuously or discontinuously increasing the ionic strength by means of a mono- or divalent alkali metal salt or alkaline earth metal salt e.g. chlorides and sulfates respectively of sodium and potassium and chlorides of magnesium and calcium or by lowering the pH value and the eluate is subsequently purified by affinity chromatography on BPTI covalently bonded to a carrier and is desorbed from the BPTI-carrier at a pH value of 4,0 to 5.0 It is preferred that the ion exchanger and, especially, the BPTI-carrier used are based on cellulose, dextran or agarose and have been crosslinked by treatment with a bifunctional reagent.

Pure kallikrein with 1000–1350 KU/mg is obtained from the organ extract, starting with 0.5–1 KU/mg, in two steps in an industrially simple and economic manner by the process described. (The kallikrein activity is determined by measurement of the hydrolysis of N-benzoyl-L-arginine ethyl ester in the embodiment standardised by the F.I.P. (Federation Internatione Pharmaceutique (International Pharmaceutical Federation)), as a titrimetric test. 1 F.I.P. unit is defined as the amount of kallikrein which splits 1 micromol of N-benzoyl-L-arginine ethyl ester at pH 8.0 and at 25° C. in one minute. Conversion into the customary kallikrein units (KU) as defined by Frey, Kraut and Werle is effected by multiplication by a factor of 6.37).

The process is divided, on the one hand into a pre-purification step on anion exchangers. In this step, the swine pancreas organ extract must be adjusted to a conductivity of 2–6 mS×cm$^{-1}$ and a pH value of 5–8. Then the crude kallikrein solution prepared is brought into contact with the ion exchanger in batch or column form and purified kallikrein is eluted from the carrier material by increasing the ionic strength by means of a mono- or di-valent alkali metal salt or alkaline earth metal salt.

The ionic strength in the pre-purification step can be increased continuously or discontinuously, in gradient form or stepwise. Alternatively, it is possible to elute kallikrein from the ion exchanger by lowering the pH value.

The use of basic ion exchangers based on cellulose for the purification of kallikrein is described in principle in U.S. Patent Specification No. 3,100,736.

Ion exchangers based on cellulose have the disadvantages of being microbiologically degradable and having a low physical stability. This restricts their use on a large industrial scale.

The use of anion exchangers based on macroporous polymers carrying basic substituents have thus also been described, in DE-OS (German Published Specification) No. 2,424,118 U.S. Patent Specification No. 3,809,748 and U.S. Patent Specification No. 4,038,141, for the purification of kallikrein. But their capacity and their purification factor for kallikrein is limited, compared with the ion exchangers based on cellulose.

According to U.S. Patent Specification No. 3,573,277, the physical properties of ion exchangers based on cellulose, "Sephadex" or "Sepharose" can be considerably improved by treatment with a bifunctional reagent, such as epichlorohydrin or 2,3-dibromopropanol. The ion exchangers modified by covalent cross-links have considerably higher flow rates than the untreated ion exchangers and can be used in column form for the purification of kallikrein.

The treatment of the anion exchangers mentioned with bifunctional reagents can take place before or after introduction of the ionic groups capable of exchange, it being preferable to carry out the treatment with the crosslinking reagent before introduction of the ion exchanger groups.

The anion exchangers used for the kallikrein purification described can be prepared either by treatment of DEAE-cellulose, DEAE-"Sephadex" (Trade Mark for dextran from Messrs. Pharmacia AB, Uppsala, Sweden) or DEAE-"Sepharose" (Trade Mark for agarose from Messrs. Pharmacia AB, Uppsala, Sweden) with bifunctional reagents, or they can be obtained commercially as crosslinked anion exchangers, such as DEAE-"Sephacel" (Trade Mark for a cellulose exchanger crosslinked with epichlorohydrin from Messrs. Pharmacia AB, Uppsala, Sweden) or DEAE-"Indion" ion exchanger (Trade Mark for a cellulose exchanger crosslinked with epichlorohydrin from Messrs. Phoenix Chemicals, Ltd., Waitaki, New Zealand).

Because of their high capacity for kallikrein, the crosslinked ion exchangers can also be used, in column form, as mixtures with inert carrier gels, such as "Sephadex" G 10, G 15 or G 25 (Trade Mark of Messrs. Pharmacia AB, Uppsala, Sweden), in various proportions for further improvement of the flow rate.

Starting from a swine pancreas organ extract with an activity of 0.5–1 KU/mg, it is possible to concentrate kallikrein to a specific activity of 15–120 KU/mg by treatment with the ion exchangers mentioned. The proteolytic activity of the swine pancreas extract in the form of the proteolytic enzymes trypsin and chymotrypsin is largely separated off.

Further purification of the kallikrein intermediate stage to give pure kallikrein is effected on a special BPTI-carrier. Starting from the organ extract, an overall purification factor of 1,000–2,500 is achieved for kallikrein. The pure kallikrein obtained has a specific activity of 1,000–1,350 KU/mg.

Polymers containing hydroxyl groups, such as "Sephadex" (Trade Mark for crosslinked insoluble dextran from Messrs. Pharmacia AB, Uppsala, Sweden), "Sepharose" (Trade Mark for insoluble agarose=a linear polysaccharide of D-galactose and 3,6-anhydro-L-galactose from Messrs. Pharmacia AB, Uppsala, Sweden) and dextran or cellulose, can be used as the polymeric carrier materials for covalent bonding of BPTI.

In order to obtain a BPTI-carrier which can be used in column form, the polymeric carrier is generally treated with a large quantity of the bifunctional reagent used for covalent bonding of the BPTI, to consolidate the carrier material by introduction of covalent cross-links.

The bifunctional reagents used are built up either symmetrically or unsymmetrically (F. Wold, Methods in Enzymology 11, page 617 et seq.). From a chemical point of view, they preferably belong to the halohydrins, bisalkyl halides, bifunctional epoxides or divinyl compounds. The following reagents may be mentioned as a representative but non-restrictive list: epichlorohydrin, epibromohydrin, dibromopropanol, 1,4-butanediol diglycidyl ether (L. sundberg and J. Porath, J. Chrom. 90 (1974), 87–98), bisoxirane and divinyl sulphone (DE-OS (German Published Specification) No. 2,312,615).

The covalent bond between the BPTI and the polymeric carrier is in all cases non-ionic and very stable. The BPTI-carrier can be used at least 50 times for the purification of kallikrein without losing its capacity for kallikrein.

The bifunctional reagents used for bonding the BPTI leads to crosslinking at the same time as bonding the BPTI. The resulting improved flow rate and improved microbial stability of the carrier material is entirely desireable from an industrial point of view.

Surprisingly, the pre-purified kallikrein fractions which are obtained from the anion exchanger and may contain salt to the extent of 1 M can be discharged onto the BPTI column without demineralisation. The optimum pH value for bonding the kallikrein is pH 6–8. Impurities can be washed out by rinsing the column with 0.2 M sodium acetate buffer of pH 6–5. Highly pure kallikrein is eluted from the BPTI-carrier below pH 5.0, but the pH value should not fall below 4,0 because of the pH-stability of kallikrein.

Surprisingly, over 99.9% of the proteolytic activity still present in the form of chymotrypsin and other proteases in the pre-purified kallikrein fraction are separated off with the resulting BPTI-carrier. This could not be predicted, since the equilibrium constants of the BPTI-kallikrein complex and of the BPTI-chymotrypsin complex are almost identical, with $6 \times 10^{-9}$ M at pH 7.2 for chymotrypsin (B. Bösterling and J. Engel, Hoppe-Seyler's Z. Physiol. Chem. 357 (1976), 1297–1307) and with $1 \times 10^{-9}$ M at pH 8.0 for kallikrein (H. Fritz, H. Schult, R. Meister and E. Werle, Hoppe-Seyler's Z. Physiol. Chem. 350 (1969), 1531–1540).

It is all the more important to separate off proteolytic activity completely from kallikrein preparations, since, according to DE-OS (German Published Specification) No. 2,442,995, there is a direct connection between the protease content of kallikrein preparations and the stability of kallikrein in solution.

The proteases are otherwise separated off in a special step by means of carrier-bonded inhibitors which are isolated from soya bean or potato and are not capable of inhibiting kallikrein.

The process according to the present invention is illustrated by the following Examples.

I EXAMPLES OF THE PRE-PURIFICATION OF THE SWINE PANCREAS ORGAN EXTRACT WITH ANION EXCHANGERS

EXAMPLE 1

Stirring of swing pancreas organ extract with untreated or modified DEAE-cellulose, in batch form (a) Preparation of the organ extract:

3.5 kg of deep-frozen swine pancreas were comminuted in a meat-mincing machine. 7 liters of tap water were added to the organ pulp and the pH value was adjusted to 4.8 with acetic acid. To de-fat the mixture, 3.5 liters $\hat{=}$ 5 kg of trichloroethylene were added, and the mixture was stirred at 25° C. for one hour. 1 kg of filtration auxiliary was added and the suspension was stirred for 15 minutes. The connective tissue was skimmed off, and residues were removed via a filter press charged with kieselguhr. The lower layer, which contained trichloroethylene, was separated off, 0.2 kg of kieselguhr was added to the aqueous phase and the solution was clarified by filtration over Seitz AS filter plates. Kallikrein yield: $0.22 \times 10^6$ KU (b) Preparation of modified DEAE-cellulose (Cl⁻ form):

45 g of DEAE-cellulose (type 130, Schleicher and Schüll GmbH, Dassel/federal Republic of Germany) were suspended in 150 ml of 1 N NaOH and, after addition of 25 ml of epichlorohydrin, were crosslinked at 60° C. for 2 hours, with stirring. The modified DEAE-cellulose was washed with distilled water, and converted into the chloride form with HCl, on a filter.

(c) Adsorption of kallikrein onto DEAE-cellulose (Cl⁻ form):

1,000 kg of pancreas organ extract prepared according to Example 1a) and having a pH value of 5.0–5.5 and a conductivity of 4.5–6.2 mS×cm⁻¹ were diluted to a conductivity of 3.0–3.3 mS×cm⁻¹ by addition of 1,500 liters of demineralised water, in a 3,000 liter kettle equipped with an anchor stirrer, and the pH value was adjusted to 7.0 by addition of 1.5–2 liters of 45% strength NaOH. 15–20 kg of moist DEAE-cellulose (chloride form), which was untreated or had been modified according to Example 1b, were added and the mixture was stirred for 60 minutes for the kallikrein to be adsorbed. The moist DEAE-cellulose was pumped at a rate of 800 liters/hour into a solid bowl centrifuge by means of a peristaltic pump, and 2,000–3,000 g were separated off from the suspension. The first runnings from the centrifuge were immediately adjusted to pH 1.8 with concentrated HCl and were stored for working up to give chymotrypsin/trypsin. To detach the kallikrein, the moist untreated or modified DEAE-cellulose separated off was stirred successively with 60, 30 and 10 liters of 0.05 M phosphate buffer of pH 5.0+0.5 M NaCl at room temperature, in each case for 60 minutes, the mixture being filtered over a Seitz single-layer filter (D=60 cm) between each operation. The combined filtrates, which had a conductivity of 32–40 mS×cm⁻¹, were adjusted to pH 7.0, with stirring, and could be applied directly to a BPTI-carrier column for the preparation of pure kallikrein.

Data for the swine pancreas organ solution (in each case per 1000 kg): protein content=8.8–15.3 kg; kallikrein activity=$28.1 \times 10^6$ KU; trypsin activity=6.0–$26.8 \times 10^6$ F.I.P. units; chymotrypsin activity: 204.5–$510.4 \times 10^6$ ATEE units (1 ATEE unit corresponds to the amount of enzyme which hydrolyses 1 micromol of N-acetyl-L-tyrosine ethyl ester/minute).

Data for the kallikrein solution pre-purified over DEAE-cellulose:

protein content: 0.552–1.34 kg; kallikrein activity=$20.9 \times 10^6$ KU=74.4%; trypsin activity: $0.1 \times 10^6$ F.I.P. units; chymotrypsin activity: 0.2–$4 \times 10^6$ ATEE units.

EXAMPLE 2

Chromatography of swine pancreas organ extract on DEAE-Sephacel (R).

A column (height=5.4 cm, diameter=8.0 cm, volume=271.3 ml) filled with DEAE-"Sephacel" was equilibrated with 0.05 M phosphate buffer of pH 7.0. 5 liters of swine pancreas extract according to Example 1(a), which had been adjusted to pH 7.0, and to a conductivity of 4.1 mS×cm⁻¹ with water, was discharged onto the column at a flow rate of 900 ml/hour. The column packing was rinsed with 3.8 liters of 0.05 M phosphate buffer of pH 7.0 and the kallikrein activity was eluted with a linear gradient of 2 liters of 0.05 M phosphate buffer of pH 7.0 to 2 liters of 0.05 phosphate buffer of pH 7.0+0.5 M NaCl.

The kallikrein activity was eluted from the column material at a conductivity of 10–12 mS×cm$^{-1}$. The active fractions were combined and demineralised by dialysis. Starting activity=172.00 KU with 45.42 g of protein Kallikrein eluate=125.256 KU with 1.4 g of protein.

II EXAMPLES OF THE PREPARATION OF THE BPTI CARRIERS

EXAMPLE 3

Preparation of "Sepharose" 4 B-epichloro-hydrin-BPTI 250 ml of sedimented "Sepharose" 4 B were suspended in 200 ml of 1 N NaOH, and were activated with 25 ml of epichlorohydrin at 60° C. for 2 hours, with stirring. The activated gel was filtered off with suction and washed on the filter several times with distilled water. The activated "Sepharose" 4 B was then suspended in 250 ml of 0.01 N NaOH, 1.25 g of BPTI with an inhibiting activity of 7100 kallikrein units=KIU/mg (kallikrein-trypsin inhibitor units, literature reference: E. K. Frey, H. Kraut and E. Werle "Das Kallikrein-Kinin-System und seine Inhibitoren" ("The kallikrein-kinin system and its inhibitors"), page 11, Ferdinand Enke Verlag, Stuttgart (1968)) were added and the suspension was stirred overnight at room temperature. The finished BPTI-carrier was filtered off, washed several times on the filter with distilled water, with 10% strength NaCl solution and again with distilled water. The filtrate contained 1.48×10$^6$ KIU, corresponding to 16.7% of the BPTI activity employed.

EXAMPLE 4

Preparation of "Sepharose" 4 B-cyanuric chloride-BPTI 500 ml of sedimented "Sepharose" 4 B were activated with 25 g of cyanuric chloride in a mixture of 250 ml of distilled water and 500 ml of dioxane at pH 5.0–7.0 for 60 minutes. The activated "Sepharose" 4 B was filtered off with suction, washed on the filter with dioxane and distilled water and coupled, as a suspension, with 5 g of added partially purified BPTI (4716 KIU/mg) at room temperature and at pH 7.0–8.0 for 16 hours. The finished BPTI-carrier was filtered off with suction and washed several times on the filter with distilled water, with 10% NaCl solution and again with water. The filtrate contained 0.25×10$^6$ KIU, corresponding to <1.1% of the BPTI activity employed.

EXAMPLE 5

Preparation of "Sepharose" 4 B-cyanogen bromide-BPTI 500 ml of sedimented "Sepharose" 4 B were activated with 4.1 g of added cyanogen bromide at a constant pH value of 11.0, with the addition of 1 N NaOH, for 30 minutes.

The pH value of the suspension was adjusted to 7.0 by addition of 2 N HCl, 5 g of partially purified BPTI (4716 KIU/mg) were added and the mixture was stirred at a constant pH and at room temperature for 16 hours.

The finished BPTI-carrier was filtered off with suction, washed several times on the filter with distilled water, with 10% strength NaCl solution and again with distilled water. The filtrate contained 11.72×10$^6$ KIU, corresponding to 49.7% of the BPTI activity employed.

EXAMPLE 6

Preparation of "Sepharose" 4 B -divinyl sulphone-BPTI 50 ml of sedimented "Sepharose " 4 B were stirred with 5 ml of divinyl sulphone in 100 ml of 0.1 M Na$_2$CO$_3$ solution at pH 11.0 and at room temperature for 2 hours.

The activated "Sepharose" 4 B was filtered off with suction, washed with distilled water and then stirred overnight with 1 g of BPTI (7100 KIU/mg) in 50 ml of 0.1 M Na$_2$CO$_3$ solution at pH 11.0.

The finished BPTI-"Sepharose" 4 B was filtered off with suction and washed on the filter with distilled water, with 10% strength NaCl solution and again with distilled water. After filtration by suction, 40.27 g of moist "Sepharose" 4 B -divinyl sulphone-BPTI were obtained. The filtrate contained 0.036×10$^6$ KIU, corresponding to 0.6% of the BPTI activity employed.

III Examples of the preparation of pure kallikrein with BPTI-carriers

EXAMPLE 7

Preparation of pure kallikrein using Sepharose 4 B$^{(R)}$ epichlorohydrin-BPTI

"Sepharose" 4 B -epichlorohydrin-BPTI-carrier prepared according to Example 3 was filled into a column (height=15 cm, diameter=37 cm, volume=16 liters). The gel bed was equilibrated with about 20 liters of 0.1 M phosphate buffer of pH 7.0 at a flow rate of 7 liters/hour.

25–50 liters of the DEAE-cellulose desorbate which had been prepared according to Example 1(c) and had been adjusted to pH 7.0 with NaOH was pumped into the column from the bottom at a flow rate of 7 liters/hour. The column was rinsed with 40 liters of 0.05 M phosphate buffer of pH 7.0+0.5 M NaCl at the same pump speed. This was followed by about 40 liters of 0.2 M sodium acetate buffer of pH 5.0–6.5 at the same flow rate until the UV absorption had reached the starting value. Kallikrein was eluted with out 40 lites of 0.05–0.3 M sodium acetate buffer of pH 4.4 and was immediately adjusted to pH 6.0–6.5 with concentrated NH$_3$ (diluted 1:1 with H$_2$O).

Adsorbed impurities were then desorbed from the BPTI-carrier with about 40 liters of 0.1 N HCl. Finally the column packing was rinsed with 40–60 liters of 0.1 M phosphate buffer of pH 7.0, until the pH value in the column runnings had risen to 7.0.

The neutralised kallikrein main runnings were desalinated on a DDS-0.36 m$^2$ laboratory module, charged with 20 DDS-600 ultrafilters, by addition of demineralised water to the recirculating liquid, and was finally concentrated to 2–3 liters, at a conductivity of the recirculating liquid of about 1 mS×cm$^{-1}$ and a kallikrein concentration of about 1000 KU/ml, and the concentrate was freezedried.

Alternatively, the kallikrein eluate could be further demineralised by dialysis or chromatography on a "Sephadex" G 25 coarse column.

DEAE-cellulose desorbate employed: 46.2 kg of solution with 316.0 g of protein; kallikrein activity: 9.46×10$^6$ KU; proteolytic activity: 632,000 Kunitz units (the protease content is measured by titration of the amino-carboxyl groups liberated when the protease-containing kallikrein solution acts on casein. A 6% solution of casein (according to Hammarsten, Merck 2242) in 0.1 N KCl was used, and titration was carried out with 0.02 N KOH at pH 9.5 and at 30° C. 1 protease unit is defined as the amount of enzyme which splits one microequivalent of peptide bond in one minute under the given conditions).

Column runnings at pH 7.0=84.9 kg with 305.1 g of protein and a kallikrein activity of $0.35 \times 10^6$ KU=3.7% of the starting activity. Rinsings from the BPTI-carrier with 0.2 M sodium acetate of pH 5.0=41.3 kg with 9.70 g of protein and a kallikrein activity of $1.43 \times 10^6$ KU≙15.1% of the starting activity.

Kallikrein eluate at pH 4.4: 39.5 kg of solution with 3.48 g of protein and a kallikrein activity of $5.61 \times 10^6$ KU≙59.3% of the activity employed.

Characterisation of the pure kallikrein:
1. Specific activity=1210 KU/mg
2. Ash content: 0.88%
3. Proteolytic activity=0.097 Kunitz units/mg=337.6 Kunitz units in total=0.05% of the proteolytic starting activity
4. Kininase content: <0.5 mg/minute/KU
5. Carboxypeptidase B (substrate: hippuryl-Arg) <0.1%
6. Carboxypeptidase A (substrate: hippuryl-Phe) <1%
7. UV absorption at 280 nm, $E_{280}^{0.1\%}=1.78$ UV absorption at 260 nm, $E_{260}^{0.1\%}=1.07$ E 280/E 260=1.66
8. Cellogel electrophoresis: The resulting kallikrein preparation consisted of kallikrein A and kallikrein B (for conditions, see U.S. Pat. No. 3,905,870). No proteins without a kallikrein activity were observed.

Maximum kallikrein capacity of the "Sepharose" 4 $B^{(R)}$ epichlorohydrin-BPTI column for the kallikrein-DEAE-cellulose intermediate stage: 800,000 KU/liter of column material.

EXAMPLE 8

Preparation of pure kallikrein with "Sepharose" 4 B -divinyl sulphone-BPTI

The "Sepharose" 4 B -divinyl sulphone-BPTI-carrier prepared in Example 6 was employed. The remaining conditions were the same as in Example 7, with the exception that rinsing of the column packing at pH 5.0 before elution of the pure kallikrein was omitted.

DEAE-cellulose desorbate employed: 25 kg of solution with 117.0 g of protein; kallikrein activity=$2.72 \times 10^6$ KU; proteolytic activity: 234,000 Kunitz units; column first runnings at pH 7.0: 87.5 kg with 126.0 g of protein and a kallikrein activity of 0 KU Kallikrein eluate at pH 4.4: 34.1 kg of solution with 3.6 g of protein and a kallikrein activity of $2.7 \times 10^6$ KU≙100% of the kallikrein activity employed.

Lyophilised pure kallikrein: 790 KU/mg; proteolytic activity=0.745 Kunitz units/mg=2682 Kunitz units=1.1% of the proteolytic starting activity.

IV COMPARISON EXAMPLES WITH OTHER BPTI-CARRIERS

EXAMPLE 9

Preparation of kallikrein using "Sepharose" 4 B -cyanuric chloride-BPTI

The "Sepharose" 4 B -cyanuric chloride-BPTI-carrier prepared according to Example 4 was filled into a column (height=8.3 cm, diameter=10.6 cm, volume=732.1 ml).

A DEAE-cellulose desorbate prepared according to Example 1(c) was discharged onto the column at a flow rate of 300 ml/hour, and further working up was carried out as described in Example 7.

Starting activity: 599,040 KU; column runnings at pH 7.0=112,944 KU≙18.8% of the starting activity; rinsings from the BPTI-carrier with 0.2 M sodium acetate buffer of pH 5.0=122,928 KU=20.5% of the starting activity: kallikrein eluate at pH 4.4: 227,430 KU=38.0% of the kallikrein activity employed; lyophilisation yield=319.2 mg with 686 KU/mg and a proteolytic activity of 0.796 Kunitz units/mg.

The specific activity and the proteolytic activity could not be improved by renewed chromatography on the BPTI-carrier.

In Cellogel electrophoresis on 40×170 mm Cellogel strips in 0.15 M phosphate buffer of pH 7.65, a more weakly acid protein band with no kallikrein activity was observed in addition to the kallikrein A and B bands.

EXAMPLE 10

Preparation of kallikrein according to DOS (German Published Specification) No. 2,363,210 using "Sepharose" 4 B -cyanogen bromide-BPTI The "Sepharose" 4 B -cyanogen bromide-BPTI-carrier prepared according to Example 5 was filled into a column (height=4.1 cm, diameter=3.6 cm, volume=41.7 ml).

750 ml of organ extract prepared according to Example 1(a) were discharged onto the column and the column was rinsed with 0.05 M phosphate buffer of pH 7.0. Impurities were eluted with 0.2 M sodium acetate buffer of pH 5.0. Kallikrein was eluted with 0.3 M sodium acetate buffer of pH 4.4. The trypsin and chymotrypsin activities were eluted from the BPTI-carrier with 0.1 N HCl.

Activity balance for kallikrein: starting activity=5700 KU; column first runnings=0 KU; kallikrein eluate=3753 KU≙65.8% of the starting activity.

Kallikrein capacity of the Sepharose 4 $B^{(R)}$-cyanogen bromide-BPTI-carrier for swine pancreas extract: 136,690 KU/liter of BPTI-carrier. Specific activity of the lyophilised kallikrein powder: 17.7 KU/mg. In Cellogel electrophoresis on 40×170 mm Cellogel strips in 0.5 M phosphate buffer of pH 7.65, 4 other more weakly acid protein bands with no kallikrein activity were observed in addition to the kallikrein A and B bands.

Activity balance for trypsin: starting activity=2025 F.I.P. units; column first runnings=0 F.I.P. units; trypsin eluate=608 F.I.P. units≙30.0% of the starting activity.

Activity balance for chymotrypsin: starting activity=244,500 ATEE units; column first runnings=204,844 ATEE units≙83.8% of the starting activity chymotrypsin eluate=0 ATEE units.

The resulting trypsin and chymotrypsin were to be designated as impure when evaluated by electrophoresis and their specific activity.

What is claimed:
1. A process for the preparation of pure kallikrein, which comprises adjusting an organ extract containing kallikrein to a conductivity of 2 to 6 mS cm$^{-1}$ at a pH value of 5 to 8, bringing the organ extract thus prepared into contact with an ion exchanger in batch form or column form, eluting the kallikrein by continuously or discontinuously increasing the ionic strength by means of a mono- or divalent alkali metal salt or alkaline earth metal salt or by lowering the pH value and subsequently purifying the eluate by affinity chromatography on BPTI covalently bonded to a carrier and then desorbing from the BPTI-carrier at a pH value of 4.0 to 5.0.

2. A process according to claim 1, in which the ion exchanger used is based on cellulose, dextran or agarose and has been crosslinked by treatment with bifunctional reagents.

3. A process according to claim 1 or 2, in which the carrier to which the BPTI is covalent bonded is based on cellulose, dextran or agarose and has been crosslinked by treatment with bifunctional reagents.

4. A process according to claim 2, in which the bifunctional reagent is a halohydrin, bis-alkyl halide, bifunctional epoxide or divinyl compound.

5. A process according to claim 3, in which the bifunctional reagent in halohydrin, bis-alkyl halide, bifunctional epoxide or divinyl compound.

* * * * *

UNITED STATES PATENT AND TRADEMARK OFFICE
CERTIFICATE OF CORRECTION

PATENT NO. : 4,393,140
DATED : Jul. 12, 1983
INVENTOR(S) : Hermann Schutt

It is certified that error appears in the above—identified patent and that said Letters Patent is hereby corrected as shown below:

Column 12, line 8, Delete "in" and insert --is a--.

Signed and Sealed this

Eighteenth Day of October 1983

[SEAL]

Attest:

GERALD J. MOSSINGHOFF

Attesting Officer

Commissioner of Patents and Trademarks